United States Patent
Hartman et al.

(10) Patent No.: US 6,651,259 B1
(45) Date of Patent: Nov. 25, 2003

(54) URINE SPECIMEN CONTAINER SYSTEM (76) Inventors: Marlene D. Hartman, 1186 Cider Press Rd., Manheim, PA (US) 17545; Gary W. Hartman, 1186 Cider Press Rd., Manheim, PA (US) 17545

( * ) Notice: Subject to any disclaimer, the term of this patent is extended or adjusted under 35 U.S.C. 154(b) by 0 days.

(21) Appl. No.: 10/159,196

(22) Filed: May 31, 2002

(51) Int. Cl.$^7$ ............................................. A47K 11/00
(52) U.S. Cl. ........................ 4/144.1; 4/144.2; 4/144.3; 604/317
(58) Field of Search ................ 4/144.1–144.4, 4/454, 455, 462–3; 604/317, 329, 331, 349; 141/331, 340, 375; 248/94

(56) References Cited

U.S. PATENT DOCUMENTS

| | | | | |
|---|---|---|---|---|
| 1,657,975 A | * | 1/1928 | Shiells | ........................ 4/144.1 |
| 1,928,170 A | * | 9/1933 | Dwork | ........................ 4/144.4 |
| 2,182,727 A | * | 12/1939 | Farrell | ............................ 4/450 |
| 2,281,727 A | * | 5/1942 | Stewart | ........................ 141/18 |
| 2,530,474 A | * | 11/1950 | Lutes | ............................. 4/483 |
| 2,591,208 A | * | 4/1952 | Seymour et al. | ................ 4/455 |
| 3,082,434 A | * | 3/1963 | Greene | ........................ 4/144.1 |
| 3,161,891 A | | 12/1964 | Bauman | |
| 3,177,500 A | | 4/1965 | Bauman | |
| 3,625,654 A | | 12/1971 | Van Duyne | |
| 3,670,342 A | * | 6/1972 | Mahony | ..................... 4/144.1 |
| 3,711,871 A | | 1/1973 | Sherin | |
| 3,811,136 A | | 5/1974 | Whitney et al. | |
| 3,878,571 A | | 4/1975 | Seeley | |
| 4,137,573 A | * | 2/1979 | Kroeger | ....................... 4/144.1 |
| 4,568,339 A | * | 2/1986 | Steer | ........................... 604/329 |
| D341,421 S | | 11/1993 | Jones | |
| 5,295,983 A | * | 3/1994 | Kubo | ........................... 604/329 |
| 5,422,076 A | | 6/1995 | Jones | |
| 5,457,823 A | * | 10/1995 | Mojena | ...................... 4/144.2 |

FOREIGN PATENT DOCUMENTS

| | | | |
|---|---|---|---|
| EP | 0296799 A1 | * 7/1985 | ............ A61G/9/00 |
| EP | 0148565 A2 | * 12/1998 | ........... A61B/10/00 |
| FR | 2456507 | 12/1980 | |

\* cited by examiner

*Primary Examiner*—Gregory L. Huson
*Assistant Examiner*—Amanda Flynn (57) ABSTRACT

A urine specimen container system is disclosed for collecting urine from a woman. The urine specimen container system includes a receiving member for receiving urine expelled from a body of a user. The receiving member has a bottom wall with a perimeter, and a peripheral wall united to the perimeter of the bottom wall to define an interior of the receiving member. The bottom wall of the receiving member has a hole formed therein for draining urine from the interior of the receiving member through a bottom surface of the bottom wall. The system includes a container having an opening with an annular lip formed about the opening. A container securing structure on the receiving member removably secures the container to the receiving member by releasably engaging the annular lip on the container.

20 Claims, 6 Drawing Sheets

Fig. 6

URINE SPECIMEN CONTAINER SYSTEM

BACKGROUND OF THE INVENTION

1. Field of the Invention

The present invention relates to urine containers and more particularly pertains to a new urine specimen container system for collecting urine from a woman.

2. Description of the Prior Art

The use of urine containers is known in the prior art. More specifically, urine containers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,161,891; U.S. Pat. No. 3,711,871; U.S. Pat. No. 3,811,136; U.S. Pat. No. 5,422,076; U.S. Pat. No. 3,625,654; and U.S. Des. Pat. No. 341,421.

While these devices fulfill their respective, particular objectives and requirements, the aforementioned patents do not disclose a new urine specimen container system of the present invention.

The urine specimen container system according to the present invention substantially departs from the conventional concepts and designs of the prior art, and in so doing provides an apparatus primarily developed for the purpose of collecting urine from a woman.

SUMMARY OF THE INVENTION

In view of the foregoing disadvantages inherent in the known types of urine containers now present in the prior art, the present invention provides a new urine specimen container system wherein the same can be utilized for collecting urine from a woman.

The general purpose of the present invention, which will be described subsequently in greater detail, is to provide a new urine specimen container system which has many of the advantages of the urine containers mentioned heretofore and many novel features that result in a new urine specimen container system which is not anticipated, rendered obvious, suggested, or even implied by any of the prior art urine containers, either alone or in any combination thereof.

To attain this, the present invention generally comprises a receiving member for receiving urine expelled from a body of a user. Thereceiving member has a bottom wall with a perimeter, and a peripheral wall united to the perimeter of the bottom wall to define an interior of the receiving member. The bottom wall of the receiving member has a hole formed therein for draining urine from the interior of the receiving member through a bottom surface of the bottom wall. A container having an opening with an annular lip formed about the opening. A container securing structure on the receiving member for removably securing the container to the receiving member by releasably engaging the annular lip on the container.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new urine specimen container system which has many of the advantages of the urine containers mentioned heretofore and many novel features that result in a new urine specimen container system which is not anticipated, rendered obvious, suggested, or even implied by any of the prior art urine containers, either alone or in any combination thereof.

It is another object of the present invention to provide a new urine specimen container system which may be easily and efficiently manufactured and marketed.

It is a further object of the present invention to provide a new urine specimen container system which is of a durable and reliable construction.

An even further object of the present invention is to provide a new urine specimen container system which is susceptible of a low cost of manufacture with regard to both materials and labor, and which accordingly is then susceptible of low prices of sale to the consuming public, thereby making such urine specimen container system economically available to the buying public.

Still yet another object of the present invention is to provide a new urine specimen container system which provides in the apparatuses and methods of the prior art some of the advantages thereof, while simultaneously overcoming some of the disadvantages normally associated therewith.

Still another object of the present invention is to provide a new urine specimen container system for collecting urine from a woman.

Yet another object of the present invention is to provide a new urine specimen container system which includes a receiving member for receiving urine expelled from a body of a user. The receiving member has a bottom wall with a perimeter, and a peripheral wall united to the perimeter of the bottom wall to define an interior of the receiving member. The bottom wall of the receiving member has a hole formed therein for draining urine from the interior of the receiving member through a bottom surface of the bottom wall. A container having an opening with an annular lip formed about the opening. A container securing structure on the receiving member for removably securing the container to the receiving member by releasably engaging the annular lip on the container.

Still yet another object of the present invention is to provide a new urine specimen container system that provides an easy method of urine collection for a woman by providing a boat-like receiving member for urinating in.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

With reference now to the drawings, and in particular to FIGS. 1 through 6 thereof, a new urine specimen container system embodying the principles and concepts of the present invention and generally designated by the reference numeral 10 will be described.

As best illustrated in FIGS. 1 through 6, the urine specimen container system 10 generally comprises a receiving member 12. The receiving member 12 has a bottom wall 13 with a bottom surface. The bottom wall 13 has a pair of side edges 14 and two end edges 16, 18. The side edges 14 preferably taper to the end edges. A peripheral wall 20 is integrally coupled to and extends upwardly from the edges 14, 16, 18. The peripheral wall 20 has a top edge 24. The peripheral wall 20 may comprise a pair of side wall sections 22 and a pair of end wall sections 23. The pair of side wall sections 22 extend substantially perpendicular to the bottom wall and the pair of end wall sections 23 extend substantially perpendicular to the bottom wall. The pair of side wall sections 22 have spaced middle portions and converging end portions such that a width between the side wall sections tapers smaller toward ends of the side wall sections. A hole 28 extends through the bottom wall 13.

In one illustrative embodiment of the invention, the bottom wall 13 has a length generally between approximately 6 and approximately 10 inches and width generally between approximately 1.5 and approximately 3 inches. The peripheral wall 20 preferably has a height generally between approximately 2 and approximately 4 inches. The receiving member 12 may be comprised of a plastic.

The receiving member may include a handle member 34 which may have a plate 34 integrally coupled to and extends away from the top edge 24 of the peripheral wall 20. The handle member 34 may include a plate that is positioned generally adjacent to the second end edge 18. The handle member 34 has a bend 36 therein such that a free end 38 of the handle member extends downwardly.

Figure 1:
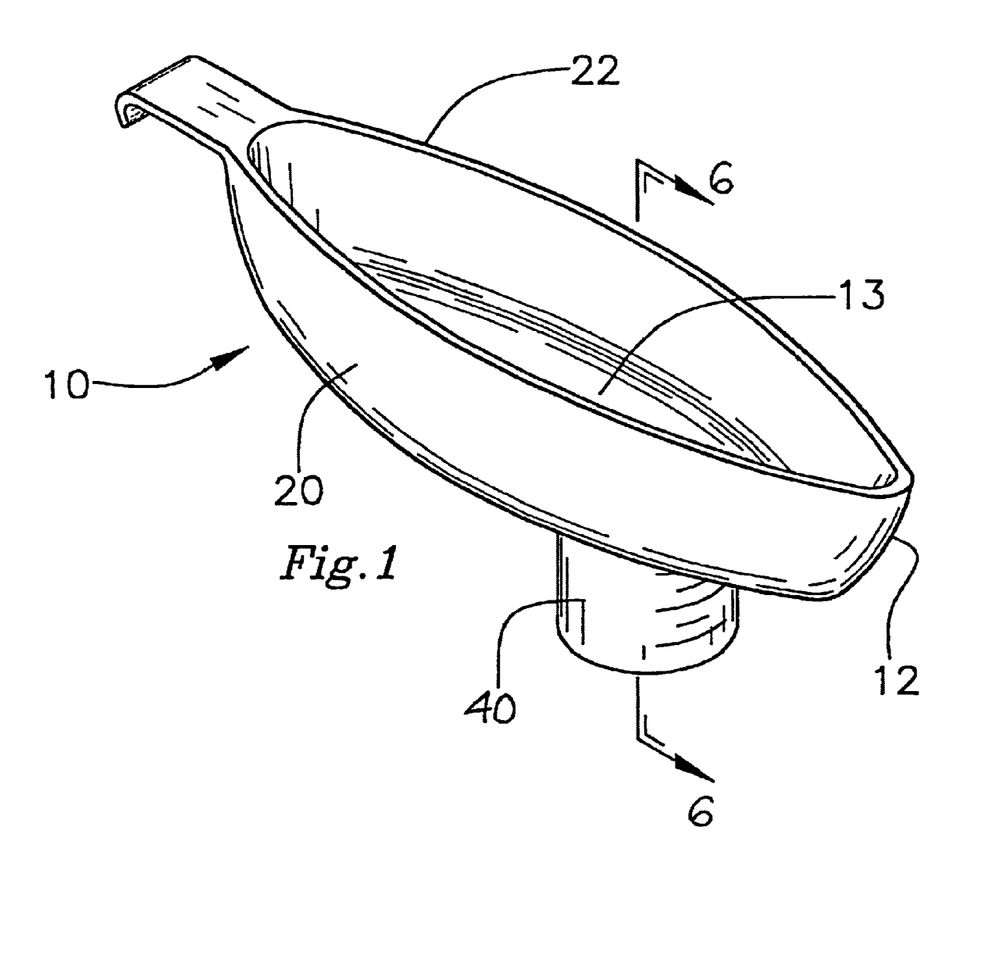
FIG. 1 is a schematic perspective view of the receiving member of a new urine specimen container system according to the present invention.
Figure 2:
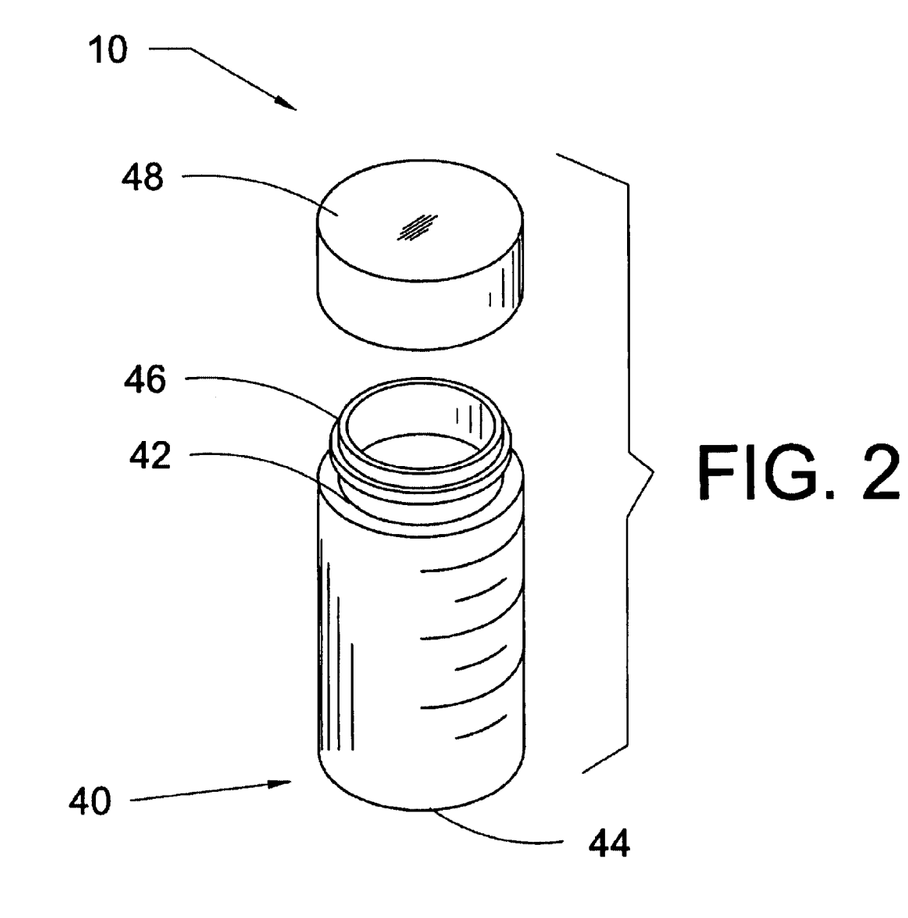
FIG. 2 is a schematic perspective view of the container of the present invention.
Figure 3:
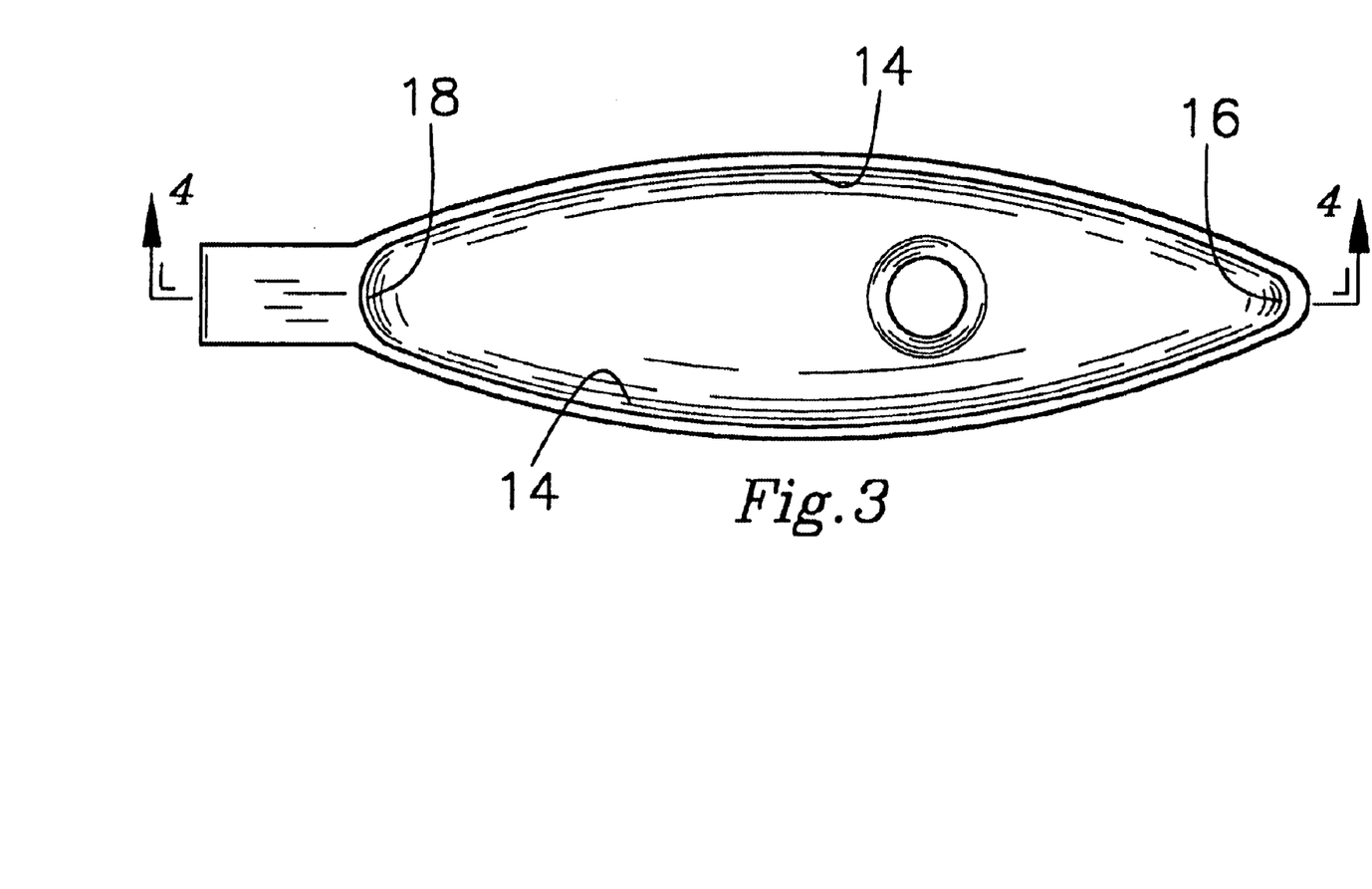
FIG. 3 is a schematic top view of the receiving member of the present invention.

A container 40 has an open side 42 and a closed side 44. The open side 42 has an annular lip 46 formed thereon The annular lip 46 is extendable into the channel 60.

Figure 4:
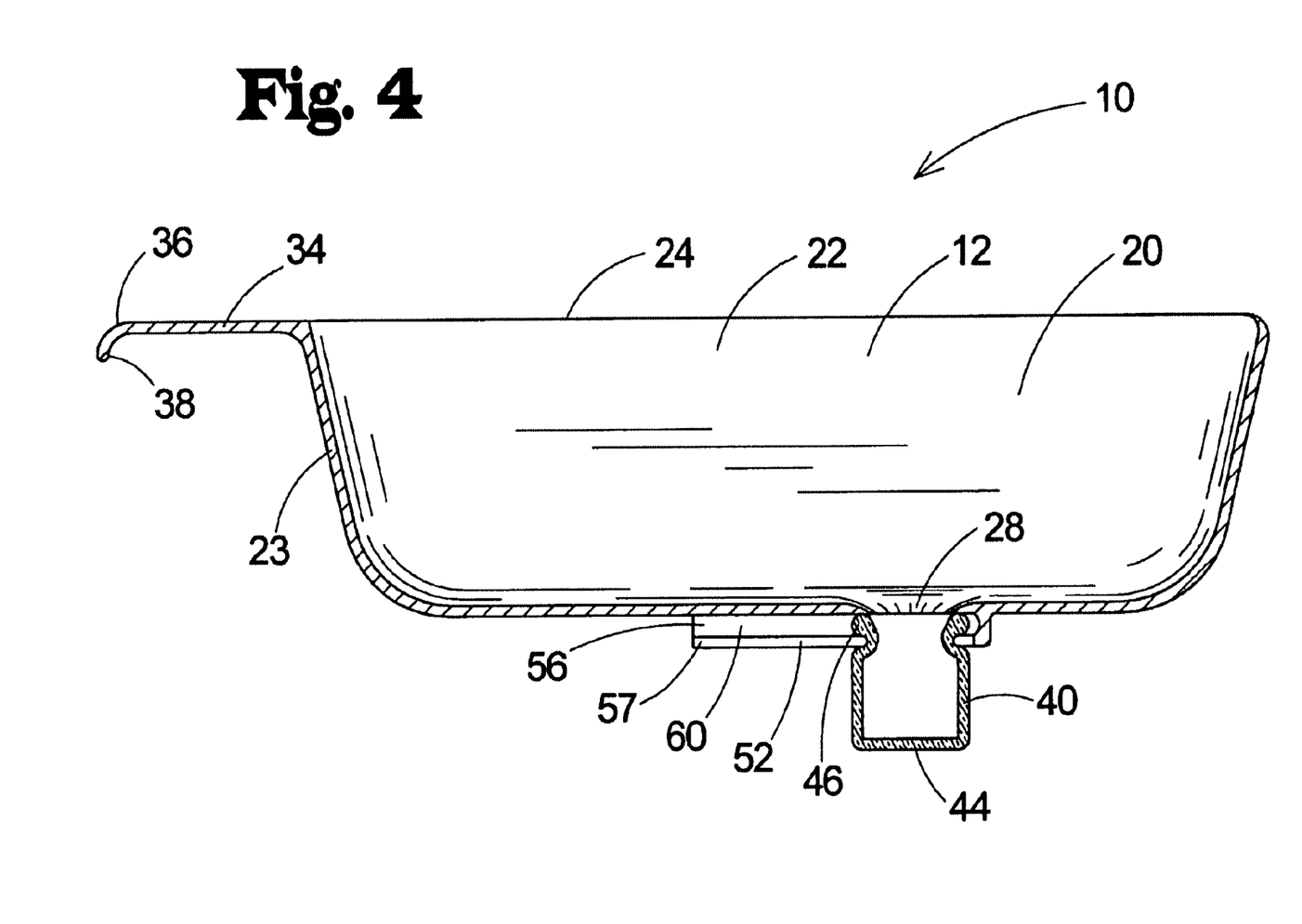
FIG. 4 is a schematic side cross-sectional view of the receiving member and container of the present invention taken along line 4—4 of FIG. 3.
Figure 5:
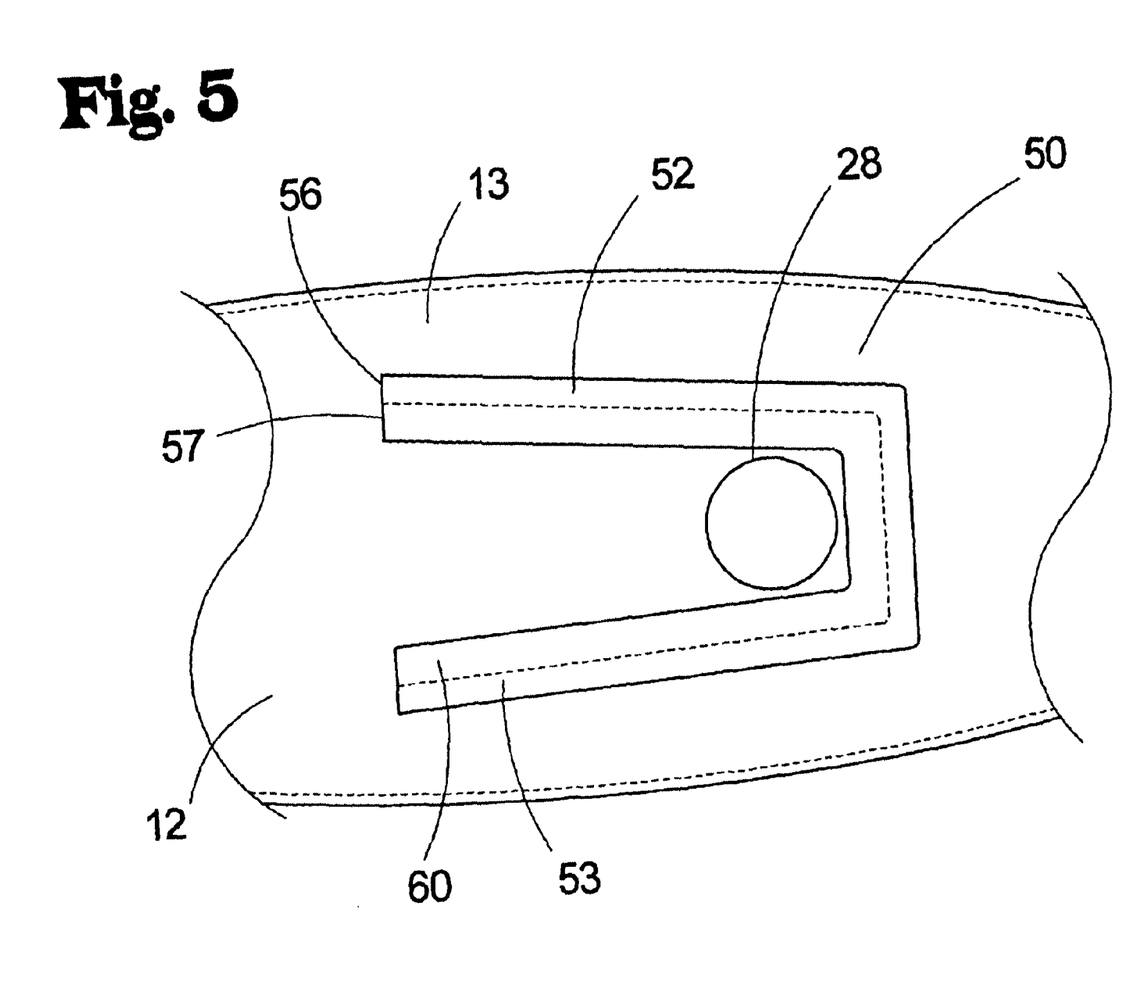
FIG. 5 is a schematic bottom view of the receiving member of the present invention.
Figure 6:
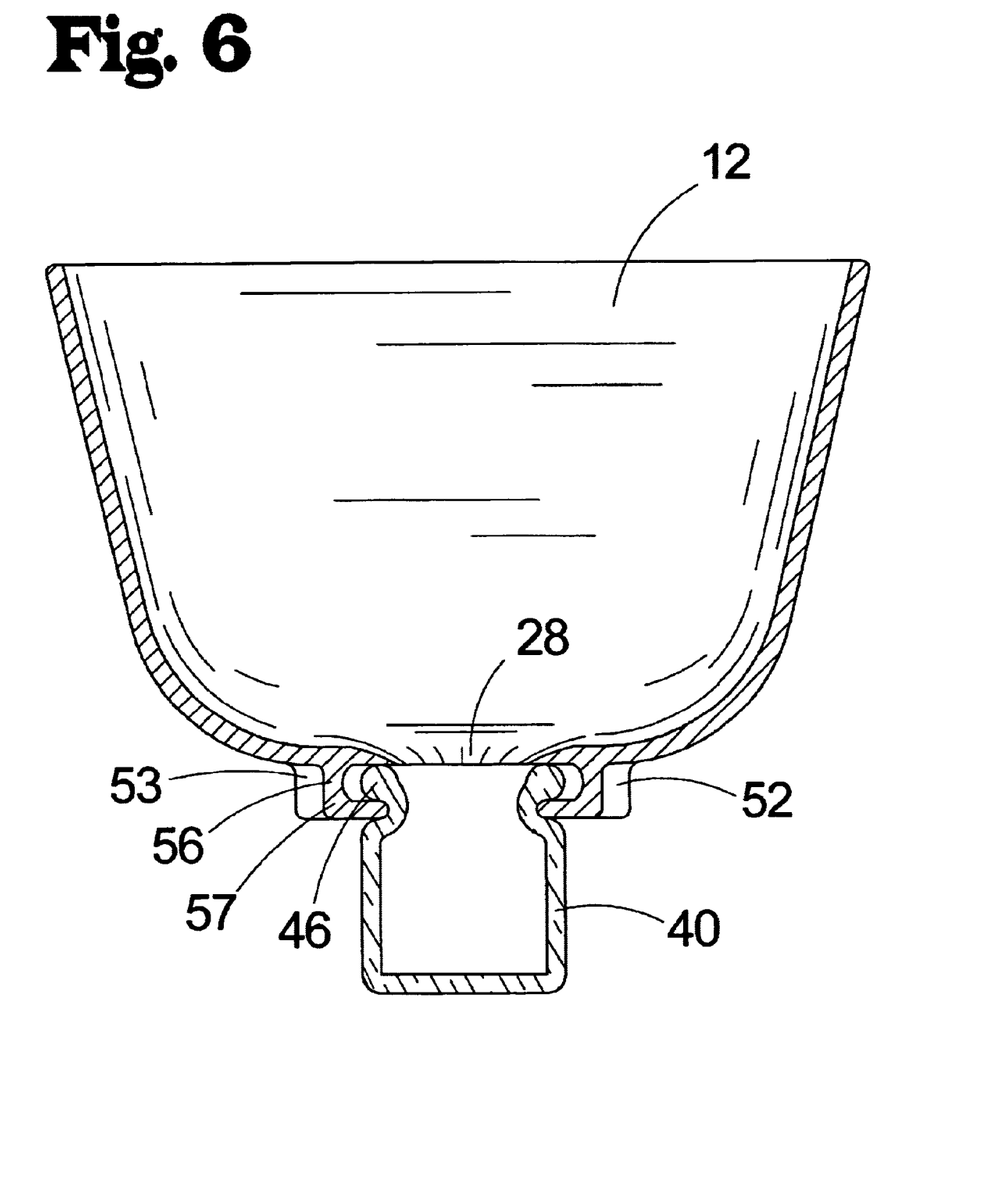
FIG. 6 is a schematic end cross-sectional view of the receiving member and container of the present invention taken along line 6—6 of FIG. 1.

Significantly, the invention includes container securing means 50 on the receiving member for removably securing the container 40 to the receiving member 12. The container securing means may be located on the bottom wall 13 adjacent to the hole 28 in the bottom wall, and may releasably engage the annular lip 46 on the container 40. The container securing means may comprise a pair of rails 52, 53 mounted on the bottom of the bottom wall 13. The rails 52, 53 may be located on opposite sides of the hole 28, and may converge towards each other near the hole and diverging away from each other away from the hole. Each of the rails 52, 53 may have a first section 56 extending away from the bottom of the bottom wall 13 and a second section 57 extending from the first section 56 toward the other of the rails. The first 56 and second 57 sections of each rail being oriented substantially perpendicularly to each other to form a channel 60 in opposition to the channel 60 formed by the other rail.

The invention may also include a cover 48 for the container 40 that is removably securable to the annular lip 46 of the container 40. The cover 48 may have an interior annular groove (not shown) that receives the annular lip 46.

In use, the container is coupled to the protruding member so that the two are fluidly coupled together. This coupling is achieved by sliding the top and annular lip of the container along the bottom of the bottom wall 13 into a position between the rails 52, 53 in the direction in which the rails converge toward each other. The portions of the annular lip 46 moves into the channel 60 of the rails 52, 53 so that the container is held against the bottom of the receiver member. The converging rails are oriented such that the container is prevented from further movement when the opening of the container is aligned with the hole in the bottom wall. The receiving member is placed below the genitalia of the person, generally a woman, who urinates in the receiving member. The urine moves through the hole and into the container which is removed from the receiving member. The container is slid away from the hole in the direction that the rails diverge to thereby release the container from the rails.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A urine specimen collector system comprising:
    a receiving member for receiving urine expelled from a body of a user, the receiving member having a bottom wall with a perimeter and a peripheral wall united to the perimeter of the bottom wall to define an interior of the receiving member, the bottom wall of the receiving member having a hole formed therein for draining urine from the interior of the receiving member through a bottom surface of the bottom wall;
    a container for storing urine collected by the receiving member, the container having an open top side and a closed bottom side, the open top side having an opening with an annular lip formed about the opening;
    container securing means on the receiving member for removably securing the container to the receiving member, the container securing means being located on the bottom wall adjacent to the hole in the bottom wall, the container securing means releasably engaging the annular lip on the container;
    wherein the container securing means comprises a pair of rails mounted on the bottom of the bottom wall, the rails being located on opposite sides of the hole;
    wherein the pair of rails converge towards each other near the hole and diverge away from each other away from the hole.

2. The system of claim 1 additionally comprising a cover for the container, the cover being removably securable to the annular lip of the container.

3. The system of claim 1 wherein each of the rails defines a channel for slidably receiving a portion of the annular lip of the container.

4. The system of claim 1 wherein the peripheral wall of the receiving member extends upwardly from the bottom wall, the peripheral wall comprising a pair of side wall section and a pair of end wall sections.

5. The system of claim 4 wherein the pair of side wall sections extend substantially perpendicular to the bottom wall and the pair of end wall sections extend substantially perpendicular to the bottom wall.

6. The system of claim 4 wherein the pair of side wall sections have spaced middle portions and converging end portions such that a width between the side wall sections tapers smaller toward ends of the side wall sections.

7. The system of claim 1 wherein the receiving member includes a handle member.

8. The system of claim 7 wherein the handle comprises a plate being mounted on the peripheral wall and extends away therefrom.

9. The system of claim 8 wherein the handle member has a bend formed therein such that a free end of the handle member extends downwardly.

10. Urine specimen collector system comprising:
    a receiving member for receiving urine expelled from a body of a user, the receiving member having a bottom wall with a perimeter and a peripheral wall united to the perimeter of the bottom wall to define an interior of the receiving member, the bottom wall of the receiving member having a hole formed therein for draining urine from the interior of the receiving member through a bottom surface of the bottom wall;
    a container for storing urine collected by the receiving member, the container having an open too side and a closed bottom side, the open top side having an opening with an annular lip formed about the opening;
    container securing means on the receiving member for removably securing the container to the receiving member, the container securing means being located on the bottom wall adjacent to the hole in the bottom wall, the container securing means releasably engaging the annular lip on the container;
    wherein the container securing means comprises a pair of rails mounted on the bottom of the bottom wall, the rails being located on opposite sides of the hole;
    wherein each of the rails has a first section extending away from the bottom of the bottom wall and a second section extending from the first section toward the other of the rails, the first and second sections of each rail being oriented substantially perpendicularly to each other to form a channel in opposition to the channel formed by the other rail for receiving opposite portions of the annular lip of the container.

11. The system of claim 10 wherein the pair of rails converge towards each other near the hole and diverge away from each other away from the hole.

12. The system of claim 10 additionally comprising a cover for the container, the cover being removably securable to the annular lip of the container.

13. The system of claim 10 wherein each of the rails defines a channel for slidably receiving a portion of the annular lip of the container.

14. The system of claim 10 wherein the peripheral wall of the receiving member extends upwardly from the bottom wall, the peripheral wall comprising a pair of side wall section and a pair of end wall sections.

15. The system of claim 14 wherein the pair of side wall sections extend substantially perpendicular to the bottom wall and the pair of end wall sections extend substantially perpendicular to the bottom wall.

16. The system of claim 14 wherein the pair of side wall sections have spaced middle portions and converging end portions such that a width between the side wall sections tapers smaller toward ends of the side wall sections.

17. The system of claim 10 wherein the receiving member includes a handle member.

18. The system of claim 17 wherein the handle comprises a plate being mounted on the peripheral wall and extends away therefrom.

19. The system of claim 18 wherein the handle member has a bend formed therein such that a free end of the handle member extends downwardly.

20. A urine specimen collector system comprising:
    a receiving member for receiving urine expelled from a body of a user, the receiving member having a bottom wall with a perimeter and a peripheral wall united to the perimeter of the bottom wall to define an interior of the receiving member, the bottom wall of the receiving member having a hole formed therein for draining urine from the interior of the receiving member through a bottom surface of the bottom wall, the peripheral wall extending upwardly from the bottom wall, the peripheral wall comprising a pair of side wall section and a pair of end wall sections, the pair of side walls sections extending substantially perpendicular to the bottom wall and the pair of end wall sections extend substantially perpendicular to the bottom wall, the pair of side wall sections having spaced middle portions and converging end portions such that a width between the side wall sections tapers smaller toward ends of the side wall sections, the peripheral wall having a top edge, the receiving member including a handle member, the handle comprising a plate being mounted on one of the end wall sections of the peripheral wall and extending away therefrom, the plate being located adjacent to the top edge of the peripheral wall, the handle member having a bend formed therein such that a free end of the handle member extends downwardly;

a container for storing urine collected by the receiving member, the container having an open top side and a closed bottom side, the open top side having an opening with an annular lip formed about the opening, the lip being extendable into the channel;

container securing means on the receiving member for removably securing the container to the receiving member, the container securing means being located on the bottom wall adjacent to the hole in the bottom wall, the container securing means releasably engaging the annular lip on the container, the container securing means comprising a pair of rails mounted on the bottom of the bottom wall, the rails being located on opposite sides of the hole, the pair of rails converging towards each other near the hole and diverging away from each other away from the hole, each of the rails having a first section extending away from the bottom of the bottom wall and a second section extending from the first section toward the other of the rails, the first and second sections of each rail being oriented substantially perpendicularly to each other to form a channel in opposition to the channel formed by the other rail; and a cover for container, the cover being removably securable to the lip of the container.

* * * * *